United States Patent
Sinharay et al.

(10) Patent No.: US 10,499,823 B2
(45) Date of Patent: Dec. 10, 2019

(54) SELECTION OF ELECTROENCEPHALOGRAPHY (EEG) CHANNELS VALID FOR DETERMINING COGNITIVE LOAD OF A SUBJECT

(71) Applicant: Tata Consultancy Services Limited, Mumbai (IN)

(72) Inventors: Arijit Sinharay, Kolkata (IN); Aniruddha Sinha, Kolkata (IN); Diptesh Das, Kolkata (IN); Debatri Chatterjee, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 756 days.

(21) Appl. No.: 14/665,476

(22) Filed: Mar. 23, 2015

(65) Prior Publication Data
US 2016/0128593 A1  May 12, 2016

(30) Foreign Application Priority Data

Nov. 6, 2014 (IN) .......................... 3498/MUM/2014

(51) Int. Cl.
  *A61B 5/04* (2006.01)
  *A61B 5/0476* (2006.01)
  (Continued)

(52) U.S. Cl.
  CPC ........ *A61B 5/04014* (2013.01); *A61B 5/0476* (2013.01); *A61B 5/165* (2013.01);
  (Continued)

(58) Field of Classification Search
  None
  See application file for complete search history.

(56) References Cited

U.S. PATENT DOCUMENTS

| 7,809,434 B2 | 10/2010 | Kofol et al. |
| 8,239,014 B2 | 8/2012 | Ochs |

(Continued)

FOREIGN PATENT DOCUMENTS

EP  2416703 A2  2/2012

*Primary Examiner* — Michael R Bloch
(74) *Attorney, Agent, or Firm* — Finnegan, Henderson, Farabow, Garrett & Dunner LLP

(57) ABSTRACT

Disclosed is a method and system for selection of Electroencephalography (EEG) channels valid for determining cognitive load of subject. According to one embodiment, EEG signals are obtained from EEG channels associated with subject performing cognitive tasks are received. Time-frequency features of EEG signals are extracted for a frequency band comprise maximum energy value, minimum energy value, average energy value, maximum frequency value, minimum frequency value, and average frequency value. Weight of an EEG channel associated with time-frequency feature is derived using statistical learning technique. Binary values for EEG channels corresponding to time-frequency feature are assigned using weight of EEG channel associated with time-frequency feature. Intersections of binary values of EEG channels corresponding to maximum energy value and average energy value, minimum energy value and average energy value, maximum frequency value and average frequency value, and minimum frequency value and average frequency value are computed. Unions of intersections are computed, wherein the unions represent EEG channels valid to determine cognitive load of subject.

19 Claims, 7 Drawing Sheets

(51) Int. Cl.
 *A61B 5/00* (2006.01)
 *A61B 5/16* (2006.01)

(52) U.S. Cl.
 CPC .......... *A61B 5/7221* (2013.01); *A61B 5/0006* (2013.01); *A61B 5/4088* (2013.01); *A61B 2560/0475* (2013.01)

(56) References Cited

U.S. PATENT DOCUMENTS

| | | |
|---|---|---|
| 2006/0111644 A1 | 5/2006 | Guttag et al. |
| 2007/0135728 A1* | 6/2007 | Snyder .................. A61B 5/048 600/544 |
| 2009/0082689 A1 | 3/2009 | Guttag et al. |

* cited by examiner

SELECTION OF ELECTROENCEPHALOGRAPHY (EEG) CHANNELS VALID FOR DETERMINING COGNITIVE LOAD OF A SUBJECT

CROSS-REFERENCE TO RELATED APPLICATIONS AND PRIORITY

This U.S. patent application claims the benefit of priority under 35 U.S.C. § 119 to India Patent Application No. 3498/MUM/2014, filed on Nov. 6, 2014. The aforementioned application is incorporated herein by reference in its entirety.

TECHNICAL FIELD

The present subject matter described herein, in general, relates to processing of bioelectric signals for diagnostic purposes, and more particularly to selection of Electroencephalography (EEG) channels of EEG device to analyze a cognitive load of a subject.

BACKGROUND

Analysis of various physiological signals to study human mental state is an emerging and widely recognized field. Cognitive load is a total amount of mental activity imposed on a memory of a subject while performing any cognitive task. Real time monitoring of the cognitive load is required in a variety of fields ranging from personalized learning to air-traffic monitoring. Mental state of the subject changes due to the cognitive load imparted on his/her brain and performance of the subject may also drastically change based on a level of the cognitive load. Physiological measurements of the subject may give more unbiased, reliable and accurate metrics than performance based indices.

Hence, analysis of brain signals is gaining increased importance. Several techniques are available to analyze the brain signals namely, Electroencephalography (EEG), functional Magnetic Resonance Imaging (fMRI), functional Near Infrared Spectroscopy (fNIRS), and the like. Neurophysiological changes in the brain to a given stimulus can be used to differentiate between human thinking processes for different levels of cognitive tasks. As compared to other available techniques, the EEG technique is relatively inexpensive, non-invasive and has excellent temporal resolution.

There are various EEG devices available in the market to measure the cognitive load of the subject. One type of the EEG devices may be high resolution EEG device which may fall under precise medical diagnostic devices and other type may be low resolution EEG devices used for Brain-Computer Interfacing (BCI) applications. The low resolution EEG devices come with lower number of EEG channels; hence often miss sensitive positions of the EEG channels related to the cognitive load. Further, the sensitive positions of the EEG channels are subjective. The sensitive positions of the EEG channels may vary from person to person or based on stimulus types.

The low resolution EEG devices come with lower number of EEG channels. Hence while determining the cognitive load of the subject, the low resolution EEG devices pose major challenges in EEG signal processing and feature extraction. While applying standard pre-processing techniques like Independent Component Analysis (ICA), Common Spatial Pattern Filtering, due to lower number of EEG channels required processing accuracy cannot be achieved. Further, complexity level in processing of the EEG signals is quite high, hence if one needs to use reduced number of EEG channels, then it is important to know valid positions of the EEG channels on the skull that give best results. Analysis for the valid positions of EEG channels can be done as a subject dependent or as a global finding (subject independent). Therefore finding the valid positions of the EEG channels plays a crucial role while determining the cognitive load by using the low resolution EEG devices. Finding the valid positions of the EEG channels is also essential for addressing variability of the subjects, variability of the stimulus and also for artifact removal from the EEG signals.

SUMMARY

This summary is provided to introduce aspects related to systems and methods for selecting a set of Electroencephalography (EEG) channels valid for determining a cognitive load of a subject, and the aspects are further described below in the detailed description. This summary is not intended to identify essential features of the claimed subject matter nor is it intended for use in determining or limiting the scope of the claimed subject matter.

In one implementation, a method for selecting a set of Electroencephalography (EEG) channels valid for determining a cognitive load of a subject is disclosed. The method comprises receiving, by a processor, EEG signals obtained from a plurality of EEG channels associated with a subject performing one or more cognitive tasks. The method further comprises extracting, by the processor, time-frequency features of the EEG signals of each EEG channel for at least one frequency band. The time-frequency features comprise at least one of a maximum energy value, a minimum energy value, an average energy value, a maximum frequency value, a minimum frequency value, and an average frequency value. The method further comprises deriving, by the processor, a weight of each EEG channel associated with each time-frequency feature using a statistical learning technique. The method further comprises assigning, by the processor, a binary value for each EEG channel corresponding to each time-frequency feature using the weight of each EEG channel associated with each time-frequency feature. The method further comprises computing, by the processor, a first intersection of the binary value of each EEG channel corresponding to the maximum energy value and the average energy value, a second intersection of the binary value of each EEG channel corresponding to the minimum energy value and the average energy value, a third intersection of the binary value of each EEG channel corresponding to the maximum frequency value and the average frequency value, and a fourth intersection of the binary value of each EEG channel corresponding to the minimum frequency value and the average frequency value. The method further comprises computing, by the processor, a first union of the first intersection and the second intersection, and a second union of the third intersection and the fourth intersection. The method further comprises computing, by the processor, a third union of the first union and the second union, wherein the third union represents a set of EEG channels valid to determine a cognitive load of the subject.

In one implementation, a system for selecting a set of Electroencephalography (EEG) channels valid for determining a cognitive load of a subject is disclosed. The system comprises a processor and a memory coupled to the processor. The processor is capable of executing programmed instructions stored in the memory to receive EEG signals obtained from a plurality of EEG channels associated with a subject performing one or more cognitive tasks. The processor further extracts time-frequency features of the EEG signals of each EEG channel for at least one frequency band. The time-frequency features comprise at least one of a maximum energy value, a minimum energy value, an average energy value, a maximum frequency value, a minimum frequency value, and an average frequency value. The processor further derives a weight of each EEG channel associated with each time-frequency feature using a statistical learning technique. The processor further assigns a binary value for each EEG channel corresponding to each time-frequency feature using the weight of each EEG channel associated with each time-frequency feature. The processor further computes a first intersection of the binary value of each EEG channel corresponding to the maximum energy value and the average energy value, a second intersection of the binary value of each EEG channel corresponding to the minimum energy value and the average energy value, a third intersection of the binary value of each EEG channel corresponding to the maximum frequency value and the average frequency value, and a fourth intersection of the binary value of each EEG channel corresponding to the minimum frequency value and the average frequency value. The processor further computes a first union of the first intersection and the second intersection, and a second union of the third intersection and the fourth intersection; and computes a third union of the first union and the second union, wherein the third union represents a set of EEG channels valid to determine a cognitive load of the subject.

In one implementation, a computer program product having embodied thereon a computer program for selecting a set of Electroencephalography (EEG) channels valid for determining a cognitive load of a subject is disclosed. The computer program product comprises a program code for receiving EEG signals obtained from a plurality of EEG channels associated with a subject performing one or more cognitive tasks. The computer program product further comprises a program code for extracting time-frequency features of the EEG signals of each EEG channel for at least one frequency band. The time-frequency features comprise at least one of a maximum energy value, a minimum energy value, an average energy value, a maximum frequency value, a minimum frequency value, and an average frequency value. The computer program product further comprises a program code for deriving a weight of each EEG channel associated with each time-frequency feature using a statistical learning technique. The computer program product further comprises a program code for assigning a binary value for each EEG channel corresponding to each time-frequency feature using the weight of each EEG channel associated with each time-frequency feature. The computer program product further comprises a program code for computing a first intersection of the binary value of each EEG channel corresponding to the maximum energy value and the average energy value, a second intersection of the binary value of each EEG channel corresponding to the minimum energy value and the average energy value, a third intersection of the binary value of each EEG channel corresponding to the maximum frequency value and the average frequency value, and a fourth intersection of the binary value of each EEG channel corresponding to the minimum frequency value and the average frequency value. The computer program product further comprises a program code for computing a first union of the first intersection and the second intersection, and a second union of the third intersection and the fourth intersection. The computer program product further comprises a program code for computing a third union of the first union and the second union, wherein the third union represents a set of EEG channels valid to determine a cognitive load of the subject.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

Figure 1:
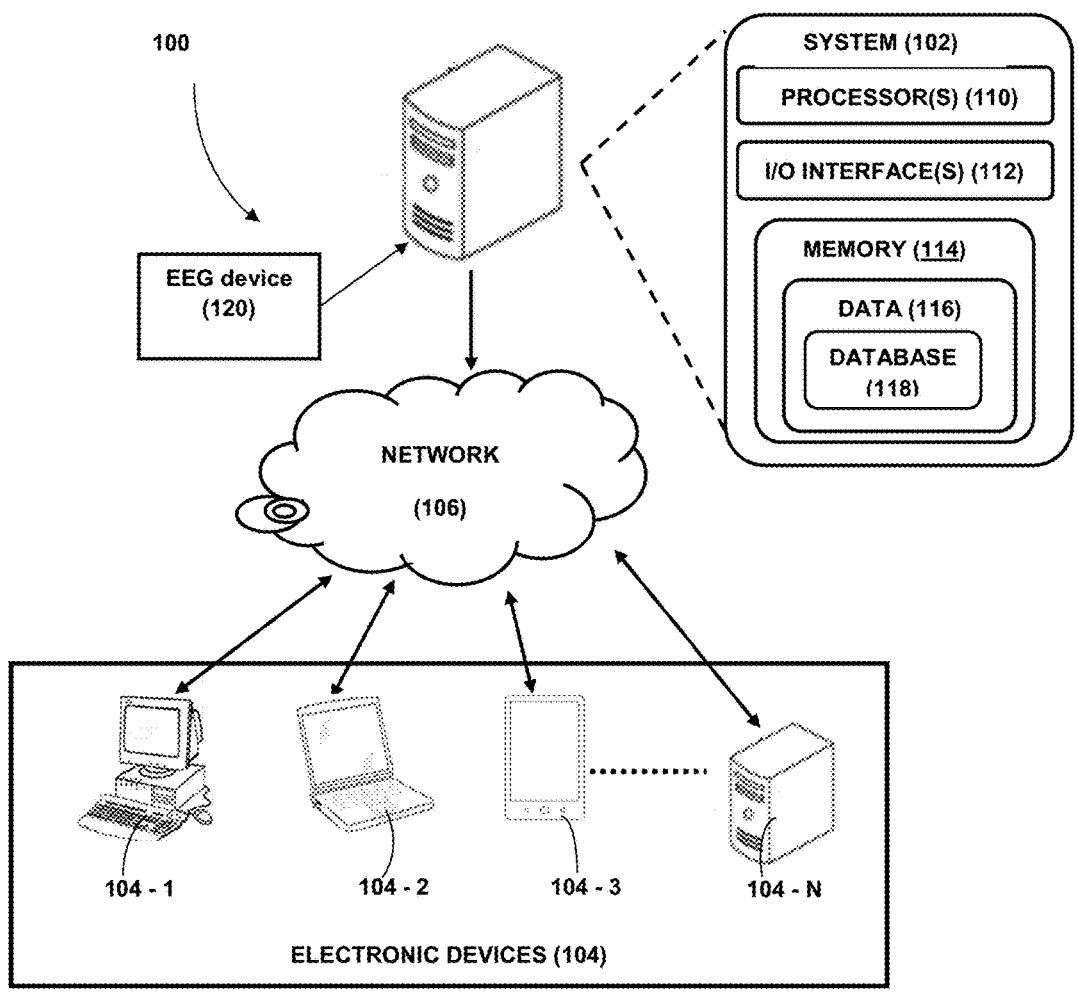
FIG. 1 illustrates a network implementation of a system for selecting a set of electroencephalography (EEG) channels valid for determining a cognitive load of a subject, in accordance with an embodiment of the present subject matter.

Systems and methods for selecting a set of Electroencephalography (EEG) channels valid for determining a cognitive load of a subject are described. The present disclosure discloses an effective and efficient mechanism for selecting the set of EEG channels of a low resolution EEG device to determine the cognitive load of the subject. In order to select the set of EEG channels, at first EEG signals obtained from a plurality of EEG channels may be received. The EEG channels may be connected to the low resolution EEG device. The EEG channels may be associated with a subject performing one or more cognitive tasks. System and method may use a standard matching test and an n-back memory test by imparting low cognitive load and high cognitive load respectively on the subject. System and method may comprise analyzing variance of at least one of alpha frequency band signals, beta frequency band signals, theta frequency band signals, and delta frequency band signals, of the EEG signals for various combinations of the EEG channels. Further time-frequency based features of the EEG signals may be extracted. The time-frequency based features of the EEG signals may be extracted from each EEG channel for at least one of the frequency bands of alpha, beta, theta and delta. The time-frequency based features may be associated with energy of the EEG signal and a frequency of the EEG signal. The time-frequency based features may comprise a maximum energy value, a minimum energy value, an average energy value, a maximum frequency value, a minimum frequency value, and an average frequency value.

Further, a weight (W) associated with each time-frequency feature of each EEG channel may be derived using a statistical learning technique. A binary value may be assigned to each EEG channel corresponding to each time-frequency feature by using the weight (W) of each EEG channel associated with each time-frequency feature respectively.

Further, a first intersection of the binary value of each EEG channel corresponding to the maximum energy value and the average energy value may be computed. A second intersection of the binary value of each EEG channel corresponding to the minimum energy value and the average energy value may be computed. A third intersection of the binary value of each EEG channel corresponding to the maximum frequency value and the average frequency value may be computed. A fourth intersection of the binary value of each EEG channel corresponding to the minimum frequency value and the average frequency value may be computed. After computing the intersections, a first union of the first intersection and the second intersection, and a second union of the third intersection and the fourth intersection may be computed.

After computing the first union and the second union, a third union of the first union and the second union may be computed. The third union may represent a set of EEG channels valid to determine a cognitive load of the subject.

While aspects of described system and method for selecting a set of Electroencephalography (EEG) channels valid for determining a cognitive load of a subject may be implemented in any number of different computing systems, environments, and/or configurations, the embodiments are described in the context of the following exemplary system.

Referring now to FIG. 1, a network implementation 100 of a system 102 for selecting a set of Electroencephalography (EEG) channels significant for determining a cognitive load of a subject is illustrated, in accordance with an embodiment of the present subject matter. In one embodiment, the system 102 provides dynamic selection of a set of EEG channels valid for determining a cognitive load of a subject. In one embodiment, the system 102 at first receives EEG signals obtained from a plurality of EEG channels. The plurality of EEG channels may be associated with a subject performing one or more cognitive tasks. Further, the system 102 may extract time-frequency features of the EEG signals received from the plurality of EEG channels. Further, the time-frequency features may be associated with at least one frequency band of the EEG signals. The frequency bands may comprise alpha, beta, theta and delta. The system 102 may further derive a weight (W) of each EEG channel associated with each time-frequency feature. The system 102 may compute plurality intersections of the binary values of the plurality of EEG channels corresponding to the time-frequency features. After computing the intersections, at least one union of the plurality of intersections may be computed. The union of the intersections may represent a set of EEG channels valid to determine a cognitive load of the subject.

Although the present subject matter is explained considering that the system 102 is implemented on a server, it may be understood that the system 102 may also be implemented in a variety of computing systems, such as a laptop computer, a desktop computer, a notebook, a workstation, a mainframe computer, a server, a network server, and the like. In one implementation, the system 102 may be implemented in a cloud-based environment. It will be understood that the system 102 may be accessed by multiple users through one or more user devices 104-1, 104-2 . . . 104-N, collectively referred to as user devices 104 hereinafter, or applications residing on the user devices 104. Examples of the user devices 104 may include, but are not limited to, a portable computer, a personal digital assistant, a handheld device, and a workstation. The user devices 104 are communicatively coupled to the system 102 through a network 106.

In one implementation, the network 106 may be a wireless network, a wired network or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 106 may include a variety of network devices, including routers, bridges, servers, computing devices, storage devices, and the like.

The system 102 is illustrated in accordance with an embodiment of the present subject matter. In one embodiment, the system 102 may include at least one processor 110, an input/output (I/O) interface 112, and a memory 114. The at least one processor 110 may be implemented as one or more microprocessors, microcomputers, microcontrollers, digital signal processors, central processing units, state machines, logic circuitries, and/or any devices that manipulate signals based on operational instructions. Among other capabilities, the at least one processor 110 is configured to fetch and execute computer-readable instructions stored in the memory 114.

The I/O interface 112 may include a variety of software and hardware interfaces, for example, a web interface, a graphical user interface, and the like. The I/O interface 112 may allow the system 102 to interact with a user directly or through the client devices 104. Further, the I/O interface 112 may enable the system 102 to communicate with other computing devices, such as web servers and external data servers (not shown). The I/O interface 112 can facilitate multiple communications within a wide variety of networks and protocol types, including wired networks, for example, LAN, cable, etc., and wireless networks, such as WLAN, cellular, or satellite. The I/O interface 112 may include one or more ports for connecting a number of devices to one another or to another server.

The memory 114 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 114 may include the programmed instructions and data 116.

The data 116, amongst other things, serves as a repository for storing data processed, received, and generated by execution of the programmed instructions. The data 116 may also include a system database 118.

In one implementation, at first, a user may use the client device 104 to access the system 102 via the I/O interface 112. The user may register using the I/O interface 112 in order to use the system 102. The working of the system 102 may be explained in detail in FIGS. 2 and 3 explained below. The system 102 may be used for selecting a set of Electroencephalography (EEG) channels valid for determining a cognitive load of a subject.

In one embodiment, in order to select the set of EEG channels valid for determining the cognitive load of the subject, the system 102 may receive EEG signals from a plurality of EEG channels. The plurality of EEG channels may be connected to an EEG device 120. In one embodiment, the EEG device 120 may be a low resolution EEG device. The plurality of EEG channels may be associated with a subject performing one or more cognitive tasks. The one or more cognitive tasks may comprise a task in which mental activity is imposed on memory of the subject. For example, the cognitive task may comprise a problem solving task, a decision making task, language skills, and the like. The EEG signals may be received from a low resolution EEG device. The low resolution EEG device may comprise a maximum of fourteen EEG channels. In another embodiment, the EEG signals may be received from a high resolution EEG device.

Cortex or cerebrum region is the largest part of a brain. The cortex or the cerebrum region is associated with different functions of the brain like critical thinking, perception, decision making and the like. Different lobes of the cortex are responsible for different cognitive functions of the brain. For example, an occipital lobe is associated with visual perception, a temporal lobe is associated with perception and recognition of an auditory stimuli and the like.

According to an exemplary embodiment, an experimental set-up for selecting the set of EEG channels valid for determining a cognitive load of a subject is described. A low resolution EEG device named 'Emotiv™' having 14-EEG channels is used. EEG signals are captured using a Python based EEG capture tool which also presents cognitive tasks to the subject and captures the EEG signals and trial video data synchronously. The EEG signals are analyzed using multiple subsets of 14 EEG (sensors) channels for specific frequency bands. Placement of the EEG channels (14 EEG channels) of the 'Emotiv™' EEG device is shown in FIG. 2.

Figure 2:
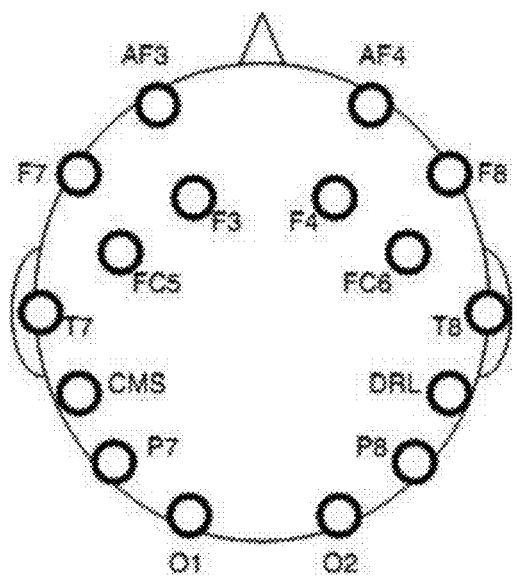
FIG. 2 illustrates placement of the EEG channels (14 EEG channels) of the 'Emotiv™' EEG device, in accordance with an embodiment of the present subject matter.

Referring to FIG. 2, the low resolution EEG device 'Emotiv™' has standard 10-20 EEG channels (electrodes). Standard referencing signals CMS (Common Mode Signal) and DRL (Driven Right Leg), placed in the location of P3 and P4, do not generate any signal and used for reference only. Remaining 14 EEG channels shown in the FIG. 2 generate the EEG signals at 128 Hz sampling rate. The EEG device has an in-built notch filter at power line frequency.

Figure 3:
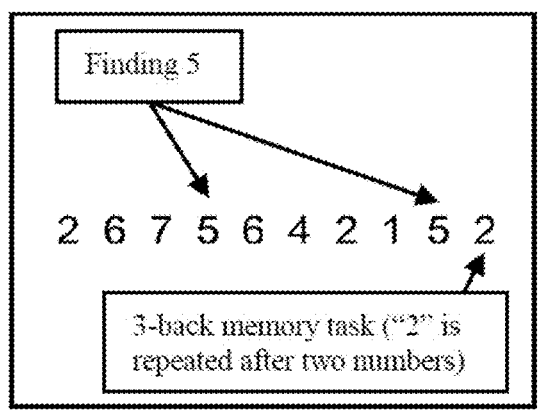
FIG. 3 illustrates experiments pertaining to a low cognitive load and a high cognitive load applied on the subjects, in accordance with an embodiment of the present subject matter.

A stimulus used by the system 102 for experimental purpose is described below. By way of an example, two elementary cognitive tasks are used for imparting a low cognitive load and a high cognitive load on the subjects (participants). A 'finding number' task is used for imparting the low cognitive load and an 'n-back memory' task is used for imparting the high cognitive load. The cognitive index may be used to measure the cognitive load imparted on the subjects while performing the cognitive task. For example, as shown in FIG. 3 two sets of experiments are designed pertaining to the low cognitive load and the high cognitive load applied on the subjects. Each experiment consisted of 10 trials. Each trial has 10 slides each, containing a number from 0 to 9. Each slide 'i' is presented for duration of 1.6 seconds.

The trials are separated by an inter trial interval of 5 seconds. The subjects are asked to relax during the inter trial interval period. The inter trial interval period is treated as a baseline period. For low load trials, termed as 'finding number', the participants are presented a set of numbers one after another. The participants are asked to respond by clicking a left mouse button if a pre-defined number (say 5) appeared on the screen as depicted in FIG. 3. For high load trials, termed as '3-back memory', the subjects needed to remember the numbers presented in each slide. The subjects are instructed to respond if a number matched with the number presented 3 slides back (as shown in FIG. 3). Two sets of trial sessions for each of the low cognitive load and the high cognitive load are conducted for each participant.

By way of an example, a group of 10 subjects are selected in age group of 25-30 years. All the subjects are right-handed male engineers working in a research lab. The selection of the subjects ensures minimum variance in level of expertise and brain lateralization across all the subjects. Each subject completed both the trial sessions of the low cognitive load and the high cognitive load with a short break of 2 minutes between each trial session termed as 'inter trial period'. Subjects are asked to relax during the 'inter trial period'. For 5 subjects the high cognitive load tasks are given first and then the low cognitive load tasks are given. For remaining 5 subjects the order of tasks is reversed. The reversing of the tasks is done to minimize a learning effect by the subjects.

The python based EEG capture tool present the stimulus to the subjects during the trials and collect the EEG signals synchronized with the trials. The python based EEG capture tool also introduces some markers in the EEG signals like an EEG start and an EEG end times, a stimulus start time, a stimulus end time, a base-line start time, a participant response time and a participant movements such as an eye-blink events and muscle motion using 'Emotiv™' Software Development Kit (SDK).

Post receiving the EEG signals, the EEG signals may be processed to remove one or more artifacts from the EEG signals. The one or more artifacts may be removed from the EEG signals using a filtering technique as disclosed in prior art. The one or more artifacts may be one or more non-cerebral artifacts. The EEG signals may be contaminated by the one or more non-cerebral artifacts. The EEG signals may be susceptible to the non-cerebral artifacts. The one or more non-cerebral artifacts may comprise artifacts not directly associated with brain activity and may be associated with other body parts. The one or more non-cerebral artifacts may comprise eye-blinks, eye movements, extra-ocular muscle activity, facial muscle movements, cardiac artifacts, and the like. The one or more non-cerebral artifacts may also comprise artifacts originated from outside the body of the subject and may be associated with a machine or an environment. The one or more non-cerebral artifacts may also comprise movement of the subject, settling of EEG electrodes, spikes originating from a momentary change in an impedance of an EEG electrode, or poor grounding of the EEG electrodes.

Post removing the one or more artifacts, time-frequency features may be extracted from the EEG signals of each EEG channel. The time-frequency features may be extracted from the EEG signals for at least one frequency band. The frequency band may be at least one of alpha ($\alpha$), beta ($\beta$), theta ($\theta$) and delta ($\delta$). The time-frequency features may comprise at least one of a maximum energy value, a minimum energy value, an average energy value, a maximum frequency value, a minimum frequency value, and an average frequency value.

Figure 4:
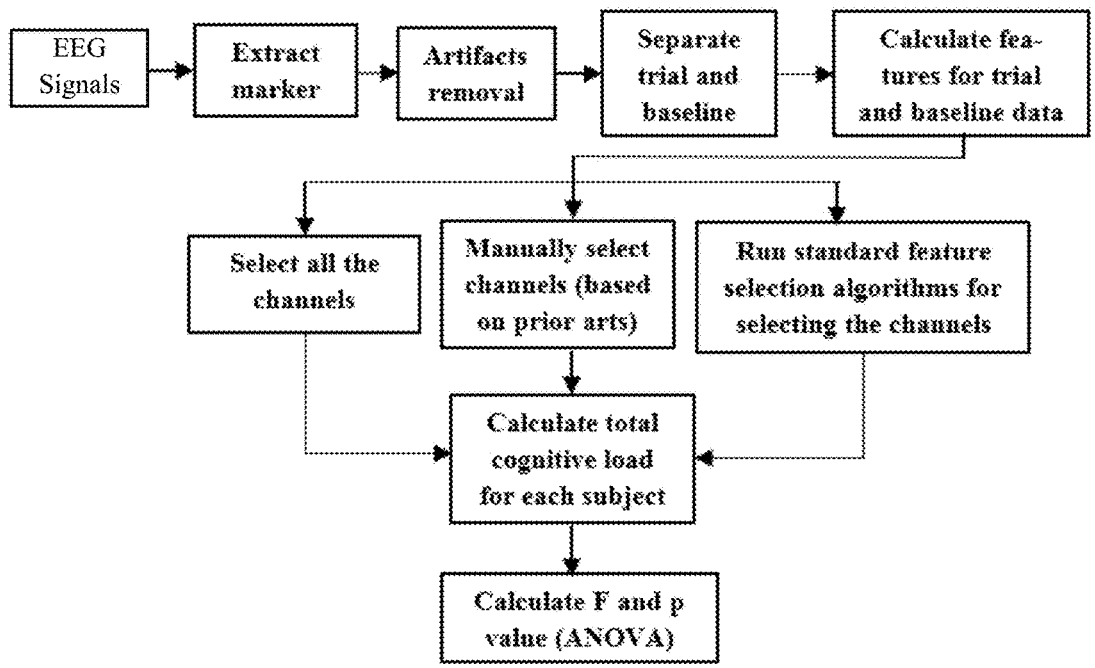
FIG. 4 illustrates a flowchart of processing of the EEG signals for selecting a set of electroencephalography (EEG) channels valid for determining a cognitive load of a subject, in accordance with an embodiment of the present subject matter.

According to another exemplary embodiment, processing of the EEG signals for removing one or more artifacts and extracting time-frequency features is explained below. Flowchart of FIG. 4 depicts processing of the EEG signals. Referring to FIG. 4, by way of an example, processing of the EEG signals for selecting the set of EEG channels to determine the cognitive load of the subject is described below. 14 time-series EEG signals (one from each EEG channel) are first segmented into individual trials. Next the individual trials are subdivided into a baseline epoch and a trial epoch as mentioned in the prior art. The division of the EEG signals into the baseline epoch and the trial epoch is done based on predefined marker data available in the EEG signals. The predefined marker data is introduced by the python based EEG capture tool. A segment corresponding to the individual trial is extracted as a fixed size window of 2.5 seconds around a response time of the subject. The trial epoch of equal length of 5 seconds is extracted for all the subjects. The baseline epoch is derived from 5 second 'inter trial interval' during which the subjects relax. Apart from the above, an analysis of continuous 5 seconds trial windows with 50% overlapping is also performed; wherein the baseline epoch is taken from the last relax time before the trial epoch window.

The EEG signals may be contaminated by the non-cerebral artifacts. The non-cerebral artifacts may be removed to remove contaminations from the EEG signals. Further, the trial epochs and the baseline epoch may be transformed using S-transform. The S-transform decomposes a non-stationary signal in a time-frequency domain for better precision.

After removing the non-cerebral artifacts, the time-frequency features may be extracted from the EEG signals for at least one frequency band. In one embodiment, the time-frequency features may be extracted from the EEG signals for at least one of alpha, beta, theta and delta frequency band. Mean frequencies and powers at the mean frequencies may be calculated for at least one of the alpha, beta, theta and delta frequency band for the EEG channels. The mean frequencies and the powers at mean frequencies for at least one of the alpha, beta, theta and delta frequency band may be used to derive a cognitive load of the subject for at least one of the alpha beta, theta and delta frequency band as mentioned in prior art. Finally, an average of the cognitive loads of each of the beta, theta and delta frequency band as selected may be calculated to get a total cognitive load. The mean frequency of the at least one of alpha, beta, theta and delta frequency band and the total cognitive load are calculated using a formula given by Anderson. The mean frequency is computed by Equation (1) given below.

$$f(\omega) = \frac{\sum_{i=0}^{n-1} I_{\omega(i)} f_{\omega(i)}}{\sum_{i=0}^{n-1} I_{\omega(i)}}$$

Equation (1)

In Equation (1), $\omega$ is a frequency band in question, n is a number of frequency bins in $\omega$, $f_{\omega(i)}$ is a frequency at bin i and $I_{\omega(i)}$ is an energy density of $\omega$ at the frequency bin i. The mean frequencies for both the trial epoch and the baseline epoch are calculated. Next frequency shift between the trial epoch and the baseline epoch are calculated. In one exemplary embodiment, the total cognitive load L(t) is calculated using a combination of a power and a frequency changes for both the alpha ($\alpha$) band and the theta ($\theta$) band from the EEG signals of the EEG channels for a trial t as mentioned in the prior art. The total cognitive load L(t) is calculated using Equation (2) given below.

$$L(t) = \Delta |f_t(\alpha)| f_t(\alpha) - \Delta |f_t(\theta)| f_t(\theta)$$

Equation (2)

Post extracting the time frequency features from the EEG signals, a weight (W) of the one or more EEG channels associated with at least one time-frequency feature may be derived using a statistical learning technique. In one embodiment, the weight (W) of each EEG channels associated with each time-frequency feature may be derived using a statistical learning technique. The weight (W) of the one or more EEG channels associated with each time-frequency feature may be derived for the at least one frequency band. The statistical learning technique may be one of a connectionist framework based Adaptive Neural Network (ANN) technique, a Maximal Information Coefficient (MIC) based technique, a minimum Redundancy Maximum Relevance (mRMR) feature selection technique, and a Hilbert-Schmidt Independence Criterion Least absolute shrinkage and selection operator technique (HSIC Lasso).

The weight (W) of the one or more EEG channels associated with at least one of time-frequency feature may be derived by using at least one of two methods—connectionist framework based on Adaptive Neural Network (ANN) and Maximal Information Coefficient (MIC) using Support Vector Machine (SVM). Derivation of the weight associated with the time-frequency feature of the EEG channel is explained below. S-transform of each epoch of the EEG signal is a time-frequency data representing the frequency response at each instance of time. The energy value (E) and the mean frequency (f) for at least one frequency band are computed for one or more EEG channels at every time instance of the epoch. The maximum, minimum and average values of E in a given epoch are termed as $E_{max}^{l,i}$, $E_{min}^{l,i}$, $E_{avg}^{l,i}$ respectively, where $i \in \{\alpha, \beta, \theta, \delta\}$ denotes frequency bands and $1 \leq l \leq 14$ denotes the 14 channels of the 'Emotiv™' device. Similarly, the maximum, minimum and average values of mean frequencies in a given epoch are termed as $f_{max}^{l,i}$, $f_{min}^{l,i}$, $f_{avg}^{l,i}$ respectively. The composite feature vector (Fr) is derived from the energy values and the mean frequency (i) of alpha ($\alpha$), beta ($\beta$), theta ($\theta$) and delta ($\delta$) frequency bands as given below in Equation (3).

$$Fr = \{E_{max}^{l,i}, E_{min}^{l,i}, E_{avg}^{l,i}, f_{max}^{l,i}, f_{min}^{l,i}, f_{avg}^{l,i}\}$$

Equation (3)

By way of an example, a feature vector $Fr \in \mathfrak{R}^{128}$ consisting $6 \times 2 \times 14 = 128$ features is calculated from 14 EEG channels of the 'Emotiv™' device. The time frequency features may be dimension features. The time frequency features of the feature vector (Fr) may further used for selection of the EEG channels. One of the objectives of the present disclosure is to find the set of EEG channels for α and θ frequency bands that maximize separation of the cognitive load L (computed using Equation (2)) for two types of tasks such as low load cognitive task and high load cognitive task.

According to an exemplary embodiment, derivation of the weight (W) associated with at least one time-frequency feature of the one or more EEG channels using a connectionist framework based on Adaptive Neural Network (ANN framework) is explained below. For example, the feature vector (Fr) calculated in Equation (3) may be used to train the ANN framework having 128 input nodes and two output nodes and a hidden layer. The number of nodes for the hidden layer may be experimentally chosen to be 25 using the method suggested by Hagiwara. Once the ANN framework is trained, then a selection layer of the ANN framework holds a set of weights ($W_k$) those are proportional to importance of the time frequency features. Though the selection layer is an integral part of the ANN framework, the selection layer holds a linear scale factor for the time frequency features.

Post deriving the weight (W) of the one or more EEG channels associated with each time-frequency feature, a binary value may be assigned to each of the one or more EEG channels corresponding to a time-frequency feature using the weight (W) of each of the one or more EEG channels associated with a time-frequency feature respectively.

The derivation of the binary values of the one or more EEG channels corresponding to the time-frequency feature may be given by Equations (4) to (9) as shown below. The derivation of the binary values for each of six types of time frequency features for the C channels may be calculated using Equations (4) to (9). If a weight (W) of an EEG channel corresponding to a time frequency feature is greater than a predefined threshold then a binary value of the EEG channel corresponding to that time frequency feature is set equal to 1 else the binary value of the EEG channel corresponding to that time frequency feature is set equal to 0. The derivation of the binary value may comprise setting the binary value of each EEG channel corresponding to at least one of the maximum energy value, the minimum energy value, the average energy value, the maximum frequency value, the minimum frequency value, and the average frequency value equal to 1, when the corresponding weight (W) associated with the maximum energy value, the minimum energy value, the average energy value, the maximum frequency value, the minimum frequency value, and the average frequency value of each EEG channel respectively is greater than a threshold value. Else the binary value is set equal to 0 for the corresponding EEG channel for corresponding time frequency feature. The binary value equal to 1 represents a valid EEG channel and the binary value equal to 0 represents not a valid EEG channel.

$$l_{E_{max}}^{i,j} = \{0,1 | l_{E_{max}}^{i,j} = 1, \text{ if } W_{E_{max}}^{i,j} \geq \eta\} \forall 1 \leq l \leq C, i \in \{\alpha,\beta,\theta,\delta\} \quad \text{Equation (4)}$$

$$l_{E_{min}}^{i,j} = \{0,1 | l_{E_{min}}^{i,j} = 1, \text{ if } W_{E_{max}}^{i,j} \geq \eta\} \forall 1 \leq l \leq C, i \in \{\alpha,\beta,\theta,\delta\} \quad \text{Equation (5)}$$

$$l_{E_{avg}}^{i,j} = \{0,1 | l_{E_{avg}}^{i,j} = 1, \text{ if } W_{E_{max}}^{i,j} \geq \eta\} \forall 1 \leq l \leq C, i \in \{\alpha,\beta,\theta,\delta\} \quad \text{Equation (6)}$$

$$l_{f_{max}}^{i,j} = \{0,1 | l_{f_{max}}^{i,j} = 1, \text{ if } W_{f_{max}}^{i,j} \geq \eta\} \forall 1 \leq l \leq C, i \in \{\alpha,\beta,\theta,\delta\} \quad \text{Equation (7)}$$

$$l_{f_{min}}^{i,j} = \{0,1 | l_{f_{min}}^{i,j} = 1, \text{ if } W_{f_{min}}^{i,j} \geq \eta\} \forall 1 \leq l \leq C, i \in \{\alpha,\beta,\theta,\delta\} \quad \text{Equation (8)}$$

$$l_{f_{avg}}^{i,j} = \{0,1 | l_{f_{avg}}^{i,j} = 1, \text{ if } W_{f_{avg}}^{i,j} \geq \eta\} \forall 1 \leq l \leq C, i \in \{\alpha,\beta,\theta,\delta\} \quad \text{Equation (9)}$$

For example, 'Emotiv™' EEG device has 14 channels, hence a value of C in Equations (4) to (9) is 14. For example, the threshold η is selected as 0.3.

After assigning binary values to each of the EEG channels for each time frequency feature, the EEG channels may be combined. The combining of the EEG channels may comprise computing one or more intersections of the binary values of the EEG channels corresponding to the time frequency features. The combining of the EEG channel may comprise computing a first intersection of the binary values of the one or more EEG channels corresponding to the maximum energy value and the average energy value. The combining of the EEG channel may further comprise computing a second intersection of the binary values of one or more EEG channels corresponding to the minimum energy value and the average energy value. The combining of the EEG channel may further comprise computing a third intersection of the binary values of the one or more EEG channels corresponding to the maximum frequency value and the average frequency value, and computing a fourth intersection of the binary value of the one or more EEG channels corresponding to the minimum frequency value and the average frequency value. The method for combining the EEG channels is given in Equations (10) to (12).

After computing the intersections of the binary values of the EEG channels, the system 102 may compute a first union of the first intersection and the second intersection, and a second union of the third intersection and the fourth intersection. After computing the first union and the second union, the system may compute a third union of the first union and the second union. The third union may represent a set of the EEG channels valid to determine a cognitive load of the subject.

According to an embodiment of the present disclosure, for combining the EEG channels, the system initially may take intersections of the EEG channels corresponding to $E_{max}^{l,i}$, $E_{avg}^{l,i}$ and $E_{min}^{l,i}$, $E_{avg}^{l,i}$ as shown in Equation (10). For combining the EEG channels, the system 102 may further take union of the two intersections such as the first intersection and the second intersection as shown in Equation (10). After computing the intersections of the binary values of the EEG channels, the system 102 may compute a first union of the first intersection and the second intersection as shown in Equation (10). In case the output of first union is empty or NULL (Φ) set, wherein there are no EEG channels selected in the first union, then the EEG channels corresponding to the average energy ($E_{avg}^{l,i}$) are considered as the output of first union as shown in Equations (10.a). Similarly for frequency (f), a third intersection of the binary values of the one or more EEG channels corresponding to the maximum frequency value $f_{max}^{l,i}$ and the average frequency value $F_{avg}^{l,i}$ may be computed, and a fourth intersection of the binary values of the one or more EEG channels corresponding to the minimum frequency value $f_{min}^{l,i}$ and the average frequency value $f_{avg}^{l,i}$ may be computed as shown in Equation (11). After computing the intersections of the binary values of the EEG channels, the system 102 may compute a second union of the third intersection and the fourth intersection as shown in Equation (11). In case the output of second union is empty or NULL (Φ) set, where are there no EEG channels selected in the second union, then the EEG channels corresponding to the average frequency ($f_{avg}^{l,i}$) are considered as the output of second union as shown in Equations (11.a).

After computing the first union and the second union, the system may compute a third union of the first union and the second union as shown in Equation (12). The third union may represent a set of the EEG channels valid to determine a cognitive load of the subject. The computation of the first intersection, the second intersection, the third intersection, and the fourth intersection may be performed for binary values of the EEG channels corresponding to time frequency features associated with frequency bands comprising at least one of alpha (α), beta (β), theta (θ) and delta (δ) as shown in Equation (10), (11), and (12). The third union of the binary values of the EEG channels may be computed for the EEG channels identified by energy and mean frequency as shown in Equation (12). The equations 10 to 12 are given below, wherein U denotes the union of sets and I denote the intersection of sets.

$$l_E^i = U(I(l_{E_{max}}^{l,i}, l_{E_{avg}}^{l,i}), I(l_{E_{min}}^{l,i}, l_{E_{avg}}^{l,i}))$$ Equation (10)

If $l_E^i == \Phi$ then $l_E^i = l_{E_{avg}}^{l,i}$ Equation (10.a)

$$l_f^i = U(I(l_{f_{max}}^{l,i}, l_{f_{avg}}^{l,i}), I(l_{f_{min}}^{l,i}, l_{f_{avg}}^{l,i}))$$ Equation (11)

If $l_f^i == \Phi$ then $l_f^i = l_{f_{avg}}^{l,i}$ Equation (11.a)

$$l^i = U(l_E^i, l_f^i) \forall i \in \{\alpha, \beta, \theta, \delta\}$$ Equation (12)

After computing the third union, the third union may represent the set of the EEG channels valid to determine the cognitive load of the subject. The set of the EEG channels valid to determine the cognitive load of the subject represents valid positions of the EEG channels on the scalp/head of the subject. For convenience, the set of the EEG channels valid to determine the cognitive load of the subject is termed as 'valid EEG channels' here onwards. Further, using Equation (2), the cognitive load (L) may be computed using the valid EEG channels valid to determine the cognitive load of the subject as provided by the third union. Further, average of the cognitive load over the valid EEG channels may be computed.

By way of an example, Table 1 to Table 3 shows experimental results of the tests conducted on 10 subjects using 'Emotiv™' EEG device having 14 channels in Equations (4) to (12), and the threshold η is selected as 0.3. Table 1 shows values of the time-frequency features' weights (normalized to 1) of 14 EEG channels associated with each time-frequency feature for alpha band using ANN based feature selection.

TABLE 1

Time-frequency features' weights (normalized to 1) of 14 EEG channels associated with each time-frequency feature for alpha band using ANN based feature selection.

| | E_max | E_min | E_avg | f_max | f_min | f_avg |
|---|---|---|---|---|---|---|
| Time-frequency Features Weights | 0.0000 | 0.0489 | 0.0689 | 0.0851 | 0.0446 | 0.0885 |
| | 0.0000 | 0.0000 | 0.0000 | 1.0000 | 1.0000 | 1.0000 |
| | 0.0142 | 0.0000 | 0.0074 | 0.0000 | 0.0000 | 0.0000 |
| | 0.9995 | 0.0801 | 0.0399 | 0.0136 | 0.0377 | 0.0207 |
| | 0.0000 | 0.0876 | 0.9985 | 1.0000 | 1.0000 | 0.0000 |
| | 0.0001 | 0.1676 | 0.0094 | 0.9800 | 0.1498 | 0.7673 |
| | 1.0000 | 1.0000 | 0.0019 | 0.9734 | 0.3291 | 0.0000 |
| | 1.0000 | 1.0000 | 1.0000 | 1.0000 | 0.0000 | 1.0000 |
| | 0.0115 | 0.9928 | 0.0000 | 0.0000 | 1.0000 | 0.0000 |
| | 1.0000 | 0.0000 | 0.0006 | 0.0001 | 0.0001 | 0.0000 |
| | 0.0000 | 0.0643 | 1.0000 | 0.0000 | 0.0000 | 0.0000 |
| | 0.9677 | 0.0000 | 0.9996 | 0.2558 | 0.0206 | 0.0002 |
| | 1.0000 | 0.7909 | 1.0000 | 0.0069 | 0.0000 | 0.0002 |
| | 0.9947 | 1.0000 | 1.0000 | 1.0000 | 1.0000 | 0.9987 |

Table 2 shows binary values assigned to 14 EEG channels associated with each time-frequency feature comparing with threshold η for 0.3 by using Equations (4) to (9).

TABLE 2

Binary values assigned to 14 EEG channels associated with each time-frequency feature comparing with threshold (η) 0.3 by using Equations (4) to (9).

| | E_max | E_min | E_avg | f_max | f_min | f_avg |
|---|---|---|---|---|---|---|
| Binary values of EEG channels | 0 | 0 | 0 | 0 | 0 | 0 |
| | 0 | 0 | 0 | 1 | 1 | 1 |
| | 0 | 0 | 0 | 0 | 0 | 0 |
| | 1 | 0 | 0 | 0 | 0 | 0 |
| | 0 | 0 | 1 | 1 | 1 | 0 |
| | 0 | 0 | 0 | 1 | 0 | 1 |
| | 1 | 1 | 0 | 1 | 1 | 0 |
| | 1 | 1 | 1 | 1 | 0 | 1 |
| | 0 | 1 | 0 | 0 | 1 | 0 |
| | 1 | 0 | 0 | 0 | 0 | 0 |
| | 0 | 0 | 1 | 0 | 0 | 0 |
| | 1 | 0 | 1 | 0 | 0 | 0 |
| | 1 | 1 | 1 | 0 | 0 | 0 |
| | 1 | 1 | 1 | 1 | 1 | 1 |

Table 3 shows results of intersection and union on the binary values of 14 EEG channels by using Equations (10) to (12)

TABLE 3

Results of intersection and union on the binary values of 14 EEG channels by using Equations (10) to (12)

| D = Intersection (1_Emax, 1_Evg) | E = Intersection (1_Emin, 1_Eavg) | F = U (D, E) – Eqn. (10) | G = Intersection (1_Fmax, 1_Favg) | H = Intersection (1_Fmin, 1_Favg) | I = U (G, H) – Eqn. (11) | I = U (F, I) – Eqn. (12) |
|---|---|---|---|---|---|---|
| 0 | 0 | 0 | 0 | 0 | 0 | 0 |
| 0 | 0 | 0 | 1 | 1 | 1 | 1 |
| 0 | 0 | 0 | 0 | 0 | 0 | 0 |
| 0 | 0 | 0 | 0 | 0 | 0 | 0 |
| 0 | 0 | 0 | 1 | 0 | 1 | 1 |
| 0 | 0 | 0 | 0 | 0 | 0 | 0 |
| 1 | 1 | 1 | 0 | 0 | 1 | 1 |
| 0 | 0 | 0 | 0 | 0 | 0 | 0 |
| 0 | 0 | 0 | 0 | 0 | 0 | 0 |
| 1 | 0 | 1 | 0 | 0 | 0 | 1 |
| 1 | 1 | 1 | 0 | 0 | 0 | 1 |
| 1 | 1 | 1 | 1 | 1 | 1 | 1 |

For example, as shown in Table 3, in column U (F, I)—Eqn. (12) shows that EEG channels Nos 2(F7), 6(P7), 8(O2), 12(F4), 13(F8), 14(AF4) are the EEG channels valid for determining the cognitive load of the subject. EEG channels No's 2(F7), 6(P7), 8(O2), 12(F4), 13(F8), 14(AF4) are positions of the EEG channels valid for determining the cognitive load of the subject.

According to an exemplary embodiment, derivation of the weight (W) of the one or more EEG channels using Maximal Information Coefficient (MIC) is explained below. The weight (W) may be derived by using Maximal Information Coefficient (MIC) with Support Vector Machine (SVM). The weight (W) of the one or more EEG channels may be associated with at least one time-frequency feature. A feature vector (Fr) of 128 dimensional features may be derived using Equation (3) and may be fed into a MIC based feature selection algorithm. MIC is a statistical tool used for measuring inter-relationship between a pair of dataset based on a concept of binning and grid formation. For every data pair (p, q), if M represents a mutual information for a grid G, then MIC of a dataset X of sample size n and grid size (p, q) less than $b_n$ is given by Equation (13).

$$\text{MIC}(X) = \max_{p,q < b_n} \{M(X)_{p,q}\} \quad \text{Equation (13), wherein } b_n = n^{0.6}$$

For different distributions of G, M(X) is given below by Equation (14).

$$M(X)_{p,q} = \frac{\max\{I(X \mid G)\}}{\log\min(p, q)} \quad \text{Equation (14)}$$

Using M(X) value (MIC value), a gain factor of the $k^{th}$ feature is defined by Equation (15).

$$W_k = \frac{1}{1 + e^{-S \cdot (m_k - 0.5)}} \quad \text{Equation (15)}$$

Referring Equation (15) S represents a stiffness factor of a sigmoid function which controls suppression and elevation of an importance of the time frequency feature. Therefore a judicious optimization of S is essential for proper evaluation of a gain factor of the individual time frequency feature. The evaluation of the gain factor of the individual time frequency feature is carried out by using SVM classifier as an optimization function. To run the SVM, an induced feature vector ($V_S$), given by Equation (16) is randomized. The induced feature vector's ($V_S$) is randomized to generate a number of dataset for manifold validation of the SVM classifier and choosing an optimum one from a series of gain factors. The randomization of the $v_S$ may be performed using the standard Randperm™ function of Matlab™ and for example a typical number (g) of randomized dataset chosen for the experiment is '4'.

$$V_S = W_S * F \quad \text{Equation (16)}$$

Referring Equation (16) $W_S$ represents the gain factor vector corresponding to stiffness value S and $V_S$ is the final induced feature vector. Based on accuracy of the SVM classifier, a Decision Parameter $DP|_S$ is generated using Equation (17). Referring Equation (17) $R_S(I)$ represents the accuracy of the SVM for a particular S and I.

$$DP|_S = \frac{\max\{R_S(I)\}}{\text{std}(R_S(I))} \forall I, \ I_i = \underset{1 \le i \le g}{\text{randperm}(r)} \quad \text{Equation (17)}$$

Final stiffness factor S and corresponding gain factor vector W can be determined as a gain factor vector associated with maximum Decision Parameter value as given in Equation (18).

$$W = W_S(S = \max(DP|_S)) \quad \text{Equation (18)}$$

Once the gain factor vector W is determined using Equation (18), selection of the set of EEG channel valid for determining a cognitive load of a subject may be done in a similar way by using values of the gain factor vector W for one or more EEG channels as subjected. Herein elements of the gain factor vector W are similar to Weights (W) as obtained in the ANN framework.

According to another embodiment, statistical analysis of the set of EEG channels selected as valid EEG channels for determining cognitive load of a subject may be performed as explained below. One-way ANOVA analysis may be used to test significant differences between cognitive loads for low load tasks and high load tasks. The one-way ANOVA analysis tests null hypothesis that two groups are derived from same population of data and hence there are no significant differences between the class means. For example, in one-way ANOVA analysis, if F value obtained is greater than 1, then the F value indicates that there is significant difference between the class means. After testing the results based on F value, the results are tested for statistical significance or p value. Smaller the p value, lesser is a chance that the test classes belong to the same group. By setting p=0.01, the F critical can be determined from a standard lookup table. F value greater than F critical denotes rejection of null hypothesis. Since, cognitive load directly depends on the frequency bands of the various EEG channels, the ANOVA analysis varies depending on the subset of EEG channels as chosen.

According to an exemplary embodiment, the system 102 may use three different ways for selecting the set of EEG channels for determining the cognitive load of the subject as depicted in FIG. 3. In first way, all the 14 EEG channels may be used. In second way manually selected EEG channels based on the prior art studies may be used. Since 'Emotiv™' device does not have any sensor at Fz or Pz locations, P7 and P8 are selected from parietal brain lobe and F3 and F4 from frontal brain lobe as P7, P8 and F3, F4 seem to be the closest representative of Pz and Fz. The total cognitive load is calculated using equation (2) considering the EEG signals from alpha band and theta band from P7, P8 and F3, F4 EEG channels only. Finally averaging the values of cognitive load calculated for P7, P8 and F3, F4 EEG channels gives the total cognitive load. Similarly, left four EEG channels of frontal brain lobe are manually selected to measure the cognitive load as explained above. In third way, a couple of feature selection algorithms are used to select valid EEG channels for at least one of alpha, beta, theta and delta frequency bands. The total cognitive load is again calculated using equation (2) but only for the EEG channels selected by the feature selection algorithms.

According to an exemplary embodiment, a comparative study of selection of the set of EEG channels by different approaches for subjecting the EEG channels and followed by an analysis of the EEG channels responsible for the cognitive load calculation are explained below. The results obtained by one-way ANOVA (Analysis of Variance) analysis, using various approaches for subjecting the EEG channels, for 10 subjects undertaking two types of tasks as described above are provided below. Table 4 shows F value and p value obtained using the one-way ANOVA analysis for the following EEG channels subsets as subjected.

The EEG channels subsets as subjected for analysis as explained here. 1) All EEG channels: Taking all 14 EEG channels of the Emotive device into account.

2) Left 4 EEG channels (Left 4): Frontal lobe of left hemisphere i.e. EEG channels AF3, F7, F3 and FC5. The frontal lobe of right hemisphere EEG channels (AF4, F8, F4 and FC6) are also used in experimentation, however they didn't produce mentionable results. The reason behind the results may be that left hemisphere is responsible for problem solving, language processing, logical thinking, planning etc.

3) Frontal and Parietal lobe (FP Lobe): Based on the finding in prior art literature, the cognitive load is calculated taking theta band from EEG channels of frontal lobe (F3, F4) and alpha band from channels of parietal lobe (P7, P8).

4) EEG channels based on prior art psycho-physiological literature (Phy 7): 7 EEG channels (Cz, P3, P4, Pz, O2, PO4, F7) which are most important for cognitive load are selected. These are used in the experiments by Tian et al. with a 32 channel EEG device. The 14-channel Emotiv™ EEG device does not have all the 7 EEG channels. In the Emotiv EEG device, the Cz, Pz are not available; P7 is used instead of P3; P8 is used instead of P4 and PO4. Hence P7, P8, O2 and F7 are used for the experiments.

5) Connectionist Framework based EEG channel selection (ANN CS): The EEG channels are selected using weights derived from the connectionist framework of ANN as explained above.

6) MIC based EEG channel selection (MIC CS): The EEG channels are selected using the weights derived from the MIC based approach as explained above.

7) Mutual Information based EEG channel selection based on prior art ([22]): As reported by Tian et al., there are global 7 EEG channels which gave good results for 3 subjects using a 32 channels EEG device. Among these, 6 EEG channels (O1, F8, F7, FC5, FC6, AF3) available in Emotiv are used.

The results of one-way ANOVA tests for different approaches for subjecting the subsets of EEG channels—considering 5 sec window around user response are given below in Table 4. The bold entries correspond to the best values of F, p and italics entries correspond to second best values of F, p for each subject. It is observed that 'MIC CS' gives best results for 4 subjects, 'Left 4' gives best results for 4 subjects and 'Phy 7' gives best results for 2 subjects.

TABLE 4

The results of one-way ANOVA tests for different approaches for subjecting the subsets of EEG channels considering 5 sec window around user response

| Subjects | All channel | Left 4 | FP Lobe | Phy 7 | ANN CS | MIC CS | [22] |
|---|---|---|---|---|---|---|---|
| S1 | F = 0.62<br>P = 0.44 | F = 9.13<br>P = 0.008 | F = 7.68<br>P = 0.014 | F = 0.014<br>P = 0.007 | F = 13.72<br>P = 0.002 | F = 18.79<br>P = 0.001 | F = 1.38<br>P = 0.25 |
| S2 | F = 3.70<br>P = 0.06 | F = 35.36<br>P = 0 | F = 11.11<br>P = 0.002 | F = 25.28<br>P = 0 | F = 4.65<br>P = 0.04 | F = 21.54<br>P = 0 | F = 19.5<br>P = 0 |
| S3 | F = 1.67<br>P = 0.21 | F = 7.37<br>P = 0.01 | F = 0.30<br>P = 0.59 | F = 12.13<br>P = 0.002 | F = 18.25<br>P = 0 | F = 24.68<br>P = 0 | F = 1.70<br>P = 0.20 |
| S4 | F = 0<br>P = 0.95 | F = 5.04<br>P = 0.03 | F = 4.56<br>P = 0.04 | F = 3.93<br>P = 0.06 | F = 1.85<br>P = 0.19 | F = 4.61<br>P = 0.04 | F = 1.49<br>P = 0.23 |
| S5 | F = 1.45<br>P = 0.24 | F = 2.07<br>P = 0.16 | F = 3.49<br>P = 0.07 | F = 11.57<br>P = 0.002 | F = 0.86<br>P = 0.36 | F = 4.61<br>P = 0.04 | F = 4.81<br>P = 0.04 |
| S6 | F = 3.84<br>P = 0.06 | F = 0.62<br>P = 0.43 | F = 2.58<br>P = 0.12 | F = 3.96<br>P = 0.06 | F = 2.03<br>P = 0.17 | F = 7.72<br>P = 0.01 | F = 1.05<br>P = 0.32 |
| S7 | F = 1.74<br>P = 0.20 | F = 19.66<br>P = 0 | F = 7.16<br>P = 0.01 | F = 13.97<br>P = 0.001 | F = 0.15<br>P = 0.70 | F = 3.21<br>P = 0.04 | F = 5.22<br>P = 0.03 |
| S8 | F = 3.94<br>P = 0.06 | F = 11.85<br>P = 0.002 | F = 3.55<br>P = 0.07 | F = 19.33<br>P = 0 | F = 12.89<br>P = 0.001 | F = 21.88<br>P = 0 | F = 19.35<br>P = 0 |
| S9 | F = 1.21<br>P = 0.28 | F = 23.64<br>P = 0 | F = 11.9<br>P = 0.001 | F = 7.13<br>P = 0.012 | F = 15.86<br>P = 0 | F = 21.13<br>P = 0 | F = 9.95<br>P = 0.004 |
| S10 | F = 0<br>P = 0.99 | F = 6.0<br>P = 0.02 | F = 2.06<br>P = 0.17 | F = 20.35<br>P = 0 | F = 6.39<br>P = 0.02 | F = 15.64<br>P = 0 | F = 0.10<br>P = 0.76 |

The output of one-way ANOVA analysis for continuous 5 seconds window with 50% overlap is shown in Table 5. The bold entries correspond to the best F values, p values and the italics entries corresponds second best F values, p values for each subject. It can be seen that for few subjects there are multiple bold entries as the F values are very close to each other. The F values in Table 5 have noticeably increased compared to the F values in Table 4. This indicates that a subject is continuously experiencing more cognitive load for the '3-back memory' task compared to the 'Finding number' task. Hence the continuous window analysis is more suitable to find the cognitive load experienced by a subject for an unknown task. It can also be seen that the 'MIC CS' gives best results for 7 subjects.

TABLE 5

Results of one-way ANOVA tests with different approaches for subjecting subsets of the EEG channels with Continuous 5 sec window with 50% overlap

| Subjects | All channel | Left 4 | FP Lobe | Phy 7 | ANN CS | MIC CS | [22] |
|---|---|---|---|---|---|---|---|
| S1 | F = 5.84<br>P = 0.017 | F = 40.36<br>P = 0 | F = 40.91<br>P = 0 | F = 45.96<br>P = 0 | F = 42.53<br>P = 0 | F = 56.2<br>P = 0 | F = 8.84<br>P = 0.003 |

TABLE 5-continued

Results of one-way ANOVA tests with different approaches for subjecting
subsets of the EEG channels with Continuous 5 sec window with 50% overlap

| Subjects | All channel | Left 4 | FP Lobe | Phy 7 | ANN CS | MIC CS | [22] |
|---|---|---|---|---|---|---|---|
| S2 | F = 15.71 | F = 58.14 | F = 33.62 | F = 58.25 | F = 17.13 | F = 56.3 | F = 37.5 |
|   | P = 0 | P = 0 | P = 0 | P = 0 | P = 0 | P = 0 | P = 0 |
| S3 | F = 0.67 | F = 32.74 | F = 7.53 | F = 40.94 | F = 42.3 | F = 47.5 | F = 0.14 |
|   | P = 0.41 | P = 0 | P = 0.006 | P = 0 | P = 0 | P = 0 | P = 0.71 |
| S4 | F = 2.29 | F = 14.73 | F = 13.41 | F = 46.8 | F = 15.9 | F = 14.77 | F = 10.82 |
|   | P = 0 | P = 0 | P = 0 | P = 0 | P = 0 | P = 0 | P = 0.001 |
| S5 | F = 20.56 | F = 16.05 | F = 22.53 | F = 19.07 | F = 18.42 | F = 0.69 | F = 6.12 |
|   | P = 0.132 | P = 0 | P = 0 | P = 0 | P = 0 | P = 0 | P = 0.014 |
| S6 | F = 7.85 | F = 2.33 | F = 9.46 | F = 33.81 | F = 0.05 | F = 53.76 | F = 0.07 |
|   | P = 0.005 | P = 0.128 | P = 0.002 | P = 0 | P = 0.814 | P = 0 | P = 0.783 |
| S7 | F = 0.12 | F = 51.71 | F = 18.87 | F = 26.34 | F = 9.36 | F = 51.73 | F = 12.68 |
|   | P = 0.732 | P = 0 | P = 0 | P = 0 | P = 0.003 | P = 0 | P = 0 |
| S8 | F = 1.77 | F = 32.44 | F = 4.58 | F = 20.54 | F = 31.5 | F = 34.6 | F = 33.67 |
|   | P = 0.185 | P = 0 | P = 0 | P = 0 | P = 0 | P = 0 | P = 0 |
| S9 | F = 3.52 | F = 45.23 | F = 23.61 | F = 18.72 | F = 31.78 | F = 48.36 | F = 20.85 |
|   | P = 0.01 | P = 0 | P = 0 | P = 0 | P = 0 | P = 0 | P = 0.001 |
| S10 | F = 5.85 | F = 20.51 | F = 1.69 | F = 13.22 | F = 0.974 | F = 35.86 | F = 3.42 |
|   | P = 0.017 | P = 0 | P = 0.195 | P = 0 | P = 0.326 | P = 0 | P = 0.066 |

Further, in order to understand repeatability of the results, another round of experiments are performed on 4 subjects out of the 7 subjects for which the F values, p values are marked as bold in 'MIC CS' column in Table 5. For another round of experiments, the previously selected EEG channels for the corresponding subjects are used. Results indicate that the trend is similar and deviation of F values is within 5% with p value <0.005.

Figure 5:
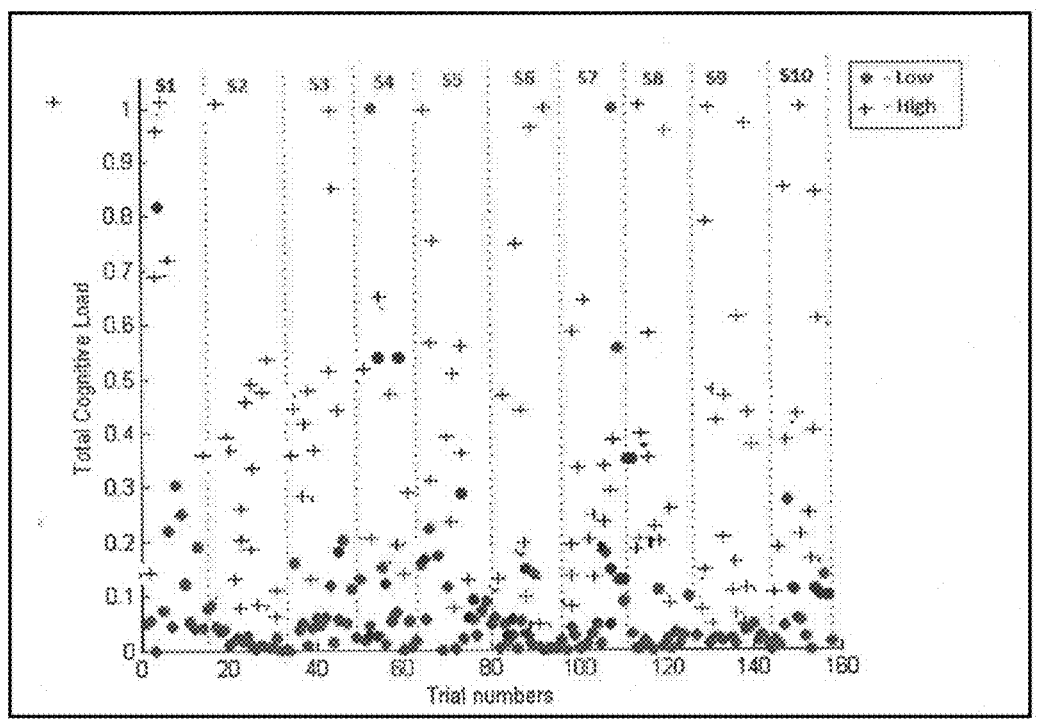
FIG. 5 illustrates pictorial representation of a total cognitive load on 10 subjects (S1 to S10) in a one-way ANOVA (Analysis of Variance) analysis, in accordance with an exemplary embodiment of the present subject matter.

Further, EEG channels subsets for each subject corresponding to the highest F values are considered and the ANOVA analysis is performed. FIG. 5 gives a pictorial representation of total cognitive load as per equation (2) for all 10 subjects (S1 to S10) considering the EEG channels having maximum F value with p<0.005, in the one-way ANOVA analysis. The 'dark square dots' represent the cognitive load corresponding to low cognitive load task (Finding number) and '+' signs correspond to high cognitive load trials/tasks (3-back memory test). The figure clearly indicates a difference in average levels for high cognitive load tasks and low cognitive load tasks for almost all 10 subjects.

The analysis of discrimination power for the selected set of the EEG channels (valid EEG channels) is explained below. The results obtained for the valid EEG channels from one-way ANOVA analysis can further be analyzed using a color map to derive insights on the discrimination power of the valid EEG channels. Binary representation of the valid EEG channels using alpha activation corresponding to maximum F value of ANOVA analysis in Table 4 is shown in Table 6, where 'S' indicates the subjects from 1 to 10 for 10 rows and columns indicate the EEG channels (1 means selected). Similar set of the valid EEG channels are derived for theta activation as well.

If the entries in the Table 6 are considered as entries of a matrix $\alpha_{ij}$, then channel activation index is defined as given by Equation (19). Referring Equation (19) N is a number of subjects (in our experiment, N=10) and j is an EEG channel index.

$$C_j = \frac{\sum_{i=1}^{N} a_{ij}}{N}, 1 \leq j \leq 14 \qquad \text{Equation (19)}$$

Table 6 provides results of EEG channels for alpha activation corresponding to maximum F value.

TABLE 6

EEG channels for alpha activation corresponding to maximum F value.

| S | AF3 | F7 | F3 | FC5 | T7 | P7 | O1 | O2 | P8 | T8 | FC6 | F4 | F8 | AF4 |
|---|---|---|---|---|---|---|---|---|---|---|---|---|---|---|
| 1 | 0 | 1 | 0 | 1 | 1 | 0 | 1 | 1 | 0 | 1 | 0 | 0 | 0 | 0 |
| 2 | 1 | 1 | 1 | 1 | 0 | 0 | 0 | 0 | 0 | 0 | 0 | 0 | 0 | 0 |
| 3 | 1 | 0 | 1 | 0 | 0 | 1 | 0 | 1 | 0 | 1 | 0 | 1 | 0 | 0 |
| 4 | 1 | 1 | 1 | 1 | 0 | 0 | 0 | 0 | 0 | 0 | 0 | 0 | 0 | 0 |
| 5 | 0 | 1 | 0 | 0 | 0 | 1 | 0 | 1 | 1 | 0 | 0 | 0 | 0 | 0 |
| 6 | 0 | 0 | 0 | 1 | 0 | 0 | 1 | 0 | 1 | 0 | 0 | 1 | 0 | 0 |
| 7 | 1 | 1 | 1 | 1 | 0 | 0 | 0 | 0 | 0 | 0 | 0 | 0 | 0 | 0 |
| 8 | 0 | 0 | 0 | 1 | 0 | 1 | 0 | 1 | 0 | 0 | 0 | 0 | 1 | 0 |
| 9 | 1 | 1 | 1 | 1 | 0 | 0 | 0 | 0 | 0 | 0 | 0 | 0 | 0 | 0 |
| 10 | 0 | 1 | 0 | 0 | 0 | 1 | 0 | 1 | 1 | 0 | 0 | 0 | 0 | 0 |

Figure 6:
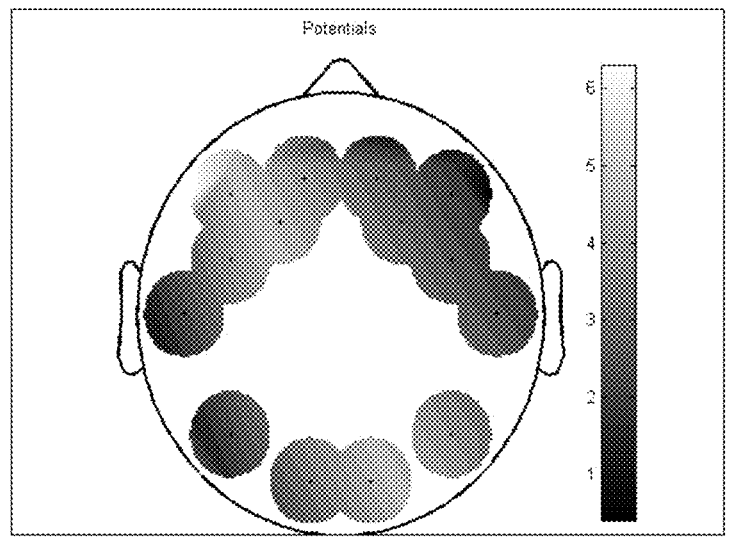
FIG. 6 illustrates an EEG channel intensity map for alpha frequency band activation, in accordance with an exemplary embodiment of the present subject matter.
Figure 7:
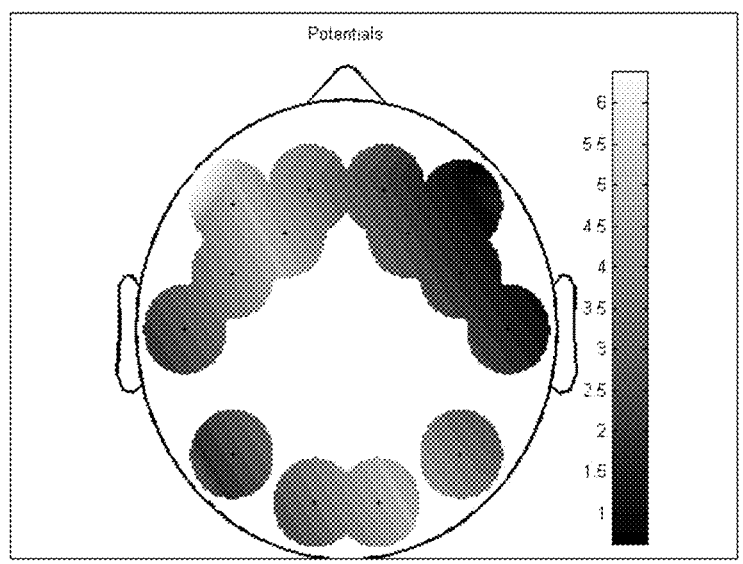
FIG. 7 illustrates an EEG channel intensity map for theta frequency band activation, in accordance with an exemplary embodiment of the present subject matter.

The $C_j$ as calculated using Equation (19) is used to plot EEG channel intensity map for alpha frequency band activation as shown in FIG. 6. Light color indicates highest and black color indicates lowest discrimination power respectively. Similarly, the EEG channel intensity map for theta frequency band activation is depicted in FIG. 7. Both the FIGS. 6 and 7 depict a strong discrimination power for left frontal lobe and partially for parieto-occipital lobe of right hemisphere.

Further, similar analysis is performed by deriving weighted channel activation index $C_j^F$: using F value as the weighing factor, shown in Equation (20). $F_i^{max}$ is maximum F value for the subject i in Table 5. It is to be noted that for each subject, the selected EEG channels in the rows of the channel selection matrix in Table 6, correspond to maximum F values of Table 5.

$$C_j^F = \frac{\sum_{i=1}^{N} a_{ij} * F_i^{max}}{N}, 1 \leq j \leq 14 \qquad \text{Equation (20)}$$

The system may further determine a weighted channel activation index of each EEG channel from the set of EEG channels to determine a discrimination power of each EEG channel. The set of EEG channels may be the valid EEG channels for determining the cognitive load of the subject. The weighted channel activation index of each EEG channel may be computed by using binary values of each EEG channel for at least one frequency band computed for a plurality of subjects and a maximum F value as a weighting factor. The F value may be greater than zero. In another embodiment, the F value may be the maximum value among the available F values for the EEG channels. Further, the F value represents a ratio of "between group variability" and "within group variability", the F value is computed using ANOVA analysis, and the F value is greater than zero.

Figure 8:
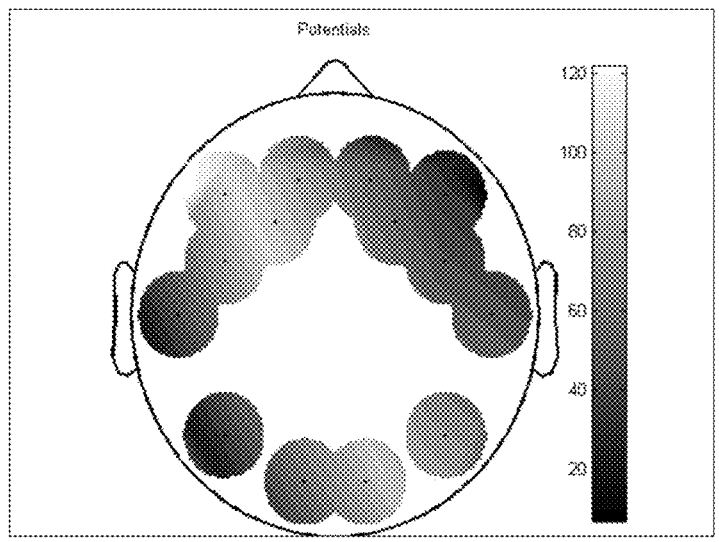
FIG. 8 illustrates discrimination power map for the EEG channel intensity using one-way ANOVA analysis F value (weighted) for alpha frequency band activation, in accordance with an exemplary embodiment of the present subject matter.
Figure 9:
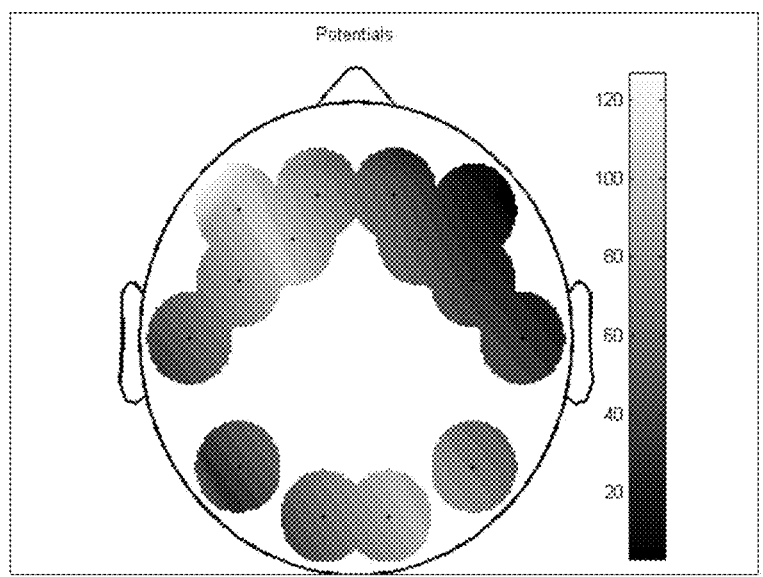
FIG. 9 illustrates discrimination power map for the EEG channels' intensity using one-way ANOVA analysis F value (weighted) for theta frequency band activation, in accordance with an exemplary embodiment of the present subject matter.

The values of $C_j^F$ are used to plot an EEG channel's intensity map for alpha frequency band and theta frequency band activation in FIG. 8 and FIG. 9 respectively. FIG. 8 and FIG. 9 shows discrimination power for the EEG channel's intensity map using one-way ANOVA (weighted) F value for (a) alpha frequency band activation and (b) theta frequency band activation respectively. FIGS. 8 and 9 also shows a strong discrimination power for left frontal lobe and partially for parieto-occipital lobe of right hemisphere. The color strength of the map provides information about importance of selection of the set of EEG channels in determination of the cognitive load using a low resolution 14-channel Emotiv™ EEG device.

Further, the system 102 plays a pivotal role in determining the cognitive load experienced by subjects while executing a particular task by selection of the EEG channels. Clear separation between different levels of cognitive loads may be achieved by optimum selection of the EEG channels. Although the present disclosure is focused on two level classifications, it can also further be extended to multilevel segregation as well. It is also evident from the above discussion that EEG channel activation is very specific to a type of the task executed and also subject dependent. The continuous window analysis with 50% overlapping provides much better result compared to the analysis around subjects' responses. The MIC based channel selection algorithm performs best for 70% of the subjects. The left frontal and right parieto-occipital channels demonstrate the most discriminative power, for the selected two types of cognitive tasks, as depicted in the map representations.

The exemplary embodiments discussed above may provide certain advantages. Though not required to practice aspects of the disclosure, these advantages may include those provided by the following features.

Some embodiments enable the system and method for providing a set of EEG channels subjected to a stimulus useful for majority (~80%) of subjects to determine cognitive load of the subjects, wherein there is no need for subject specific training of the EEG channels while using the set of EEG channels.

Some embodiments enable the system and the method for providing a method of intersection and union to derive valid EEG channels to determine cognitive load of a subject.

Some embodiments enable the system and the method for providing Maximal Information Coefficient based selection of a set of EEG channels for determining a cognitive load of a subject using low cost low resolution EEG devices.

Some embodiments enable the system and the method for reducing processing load/complexity due to usage of selected number of EEG channels in real-time set-up.

Figure 10:
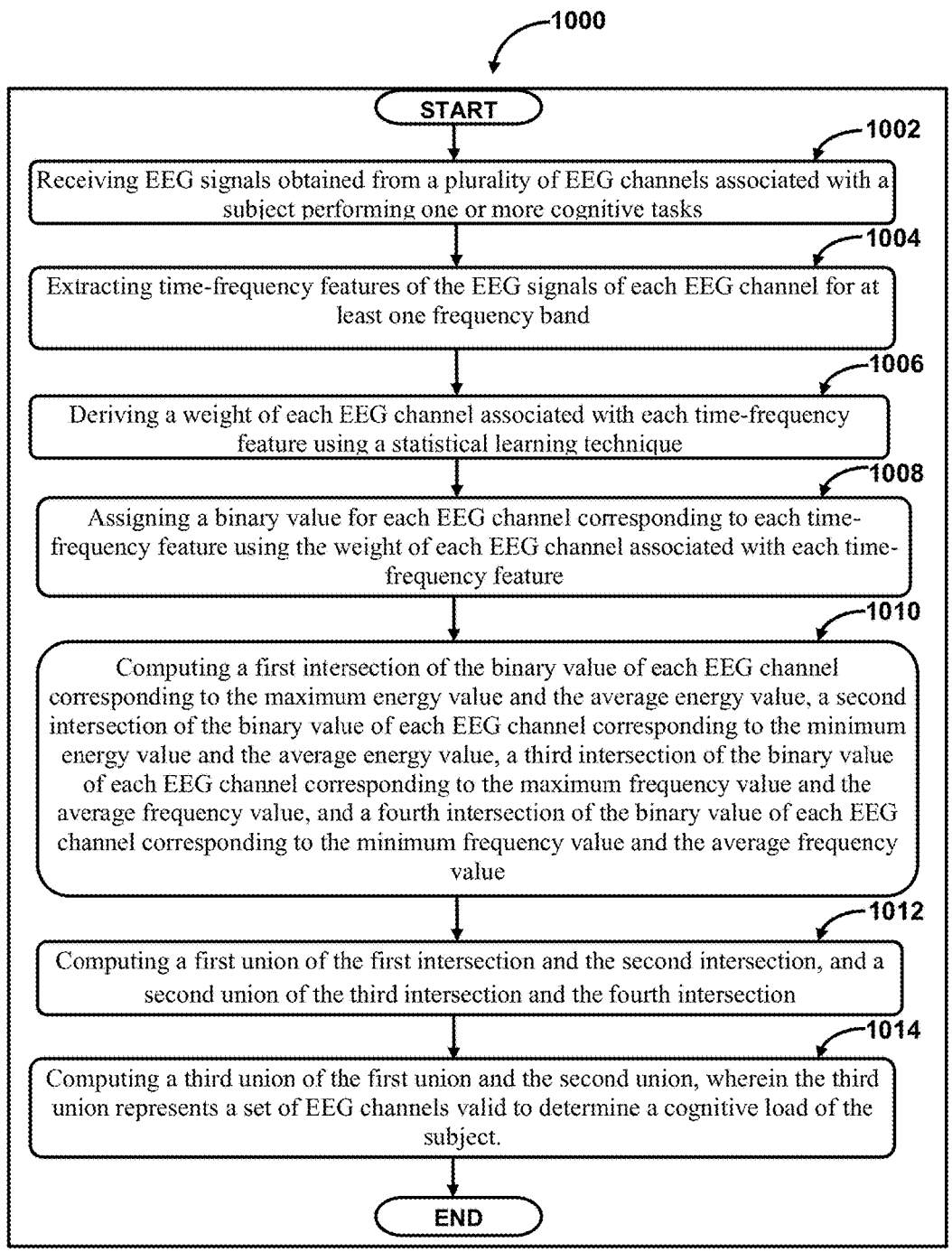
FIG. 10 illustrates a flowchart of a method for selecting a set of electroencephalography (EEG) channels valid for determining cognitive load of a subject, in accordance with an embodiment of the present subject matter.

Referring now to FIG. 10, a method 1000 for dynamically generating a playlist of multimedia files based upon user's mood is shown, in accordance with an embodiment of the present subject matter. The method 1000 may be described in the general context of computer executable instructions. Generally, computer executable instructions can include routines, programs, objects, components, data structures, procedures, modules, functions, etc., that perform particular functions or implement particular abstract data types. The method 1000 may also be practiced in a distributed computing environment where functions are performed by remote processing devices that are linked through a communications network. In a distributed computing environment, computer executable instructions may be located in both local and remote computer storage media, including memory storage devices.

The order in which the method 1000 is described is not intended to be construed as a limitation, and any number of the described method blocks can be combined in any order to implement the method 1000 or alternate methods. Additionally, individual blocks may be deleted from the method 1000 without departing from the spirit and scope of the subject matter described herein. Furthermore, the method can be implemented in any suitable hardware, software, firmware, or combination thereof. However, for ease of explanation, in the embodiments described below, the method 1000 may be considered to be implemented in the above described system 102.

At block 1002, EEG signals obtained from a plurality of EEG channels associated with a subject performing one or more cognitive tasks may be received. The EEG signals may be processed initially to remove one or more artifacts from the EEG signals. The plurality of EEG channels may be connected to a low resolution EEG device. The one or more cognitive tasks may comprise low load cognitive tasks and high load cognitive tasks.

At block 1004, time-frequency features of the EEG signals of each EEG channel for at least one frequency band may be extracted. The time-frequency features may comprise at least one of a maximum energy value, a minimum energy value, an average energy value, a maximum frequency value, a minimum frequency value, and an average frequency value. The frequency band of the EEG channels may be at least one of alpha, beta, theta and delta.

At block 1006, a weight of each EEG channel associated with each time-frequency feature may be derived using a statistical learning technique. The statistical learning technique may be one of a connectionist framework based Adaptive Neural Network technique, and Maximal Information Coefficient (MIC) based technique, a minimum Redundancy Maximum Relevance (mRMR) feature selection technique, and a Hilbert-Schmidt Independence Criterion Least absolute shrinkage and selection operator technique (HSIC Lasso).

At block 1008, a binary value for each EEG channel corresponding to each time-frequency feature may be assigned using the weight of each EEG channel associated with each time-frequency feature. The binary value of each EEG channel corresponding to each time-frequency feature may be derived for each EEG channel for the at least one frequency band using the weight associated with each time-frequency feature of each EEG channel for the at least one frequency band respectively. Assigning of the binary value may further comprise setting the binary value of each EEG channel for the at least one frequency band corresponding to each of the maximum energy value, the minimum energy value, the average energy value, the maximum frequency value, the minimum frequency value, and the average frequency value equal to 1, when the corresponding weight associated with the maximum energy value, the minimum energy value, the average energy value, the maximum frequency value, the minimum frequency value, and the average frequency value of each EEG channel for the at least one frequency band respectively is greater than a threshold value, else the binary value is set equal to 0. The binary value equal to 1 may represent a valid EEG channel and the binary value equal to 0 represents a not valid EEG channel.

At block 1010, a first intersection of the binary value of each EEG channel corresponding to the maximum energy value and the average energy value may be computed, a second intersection of the binary value of each EEG channel corresponding to the minimum energy value and the average energy value may be computed, a third intersection of the binary value of each EEG channel corresponding to the maximum frequency value and the average frequency value may be computed, and a fourth intersection of the binary value of each EEG channel corresponding to the minimum frequency value and the average frequency value may be computed.

At block 1012, a first union of the first intersection and the second intersection may be computed, and a second union of the third intersection and the fourth intersection may be computed.

At block 1014, a third union of the first union and the second union may be computed. The third union may represent a set of EEG channels valid to determine a cognitive load of the subject. The third union having binary values equal to 1 may represent the set of EEG channels valid to determine the cognitive load of the subject.

The method 1000 may further comprise determining a weighted channel activation index of each EEG channel from the set of EEG channels to determine a discrimination power of each EEG channel. The weighted channel activation index of each EEG channel may be computed by using binary values of each EEG channel for at least one frequency band computed for a plurality of subjects and a maximum F value as a weighting factor. The F value may be greater than zero. In another embodiment, the F value may be the maximum value among the available F values for the EEG channels. Further, the F value may represent a ratio of "between group variability" and "within group variability", and the F value may be computed using ANOVA analysis.

Although implementations for methods and systems for selecting a set of Electroencephalography (EEG) channels valid for determining a cognitive load of a subject have been described in language specific to structural features and/or methods, it is to be understood that the appended claims are not necessarily limited to the specific features or methods described. Rather, the specific features and methods are disclosed as examples of implementations for selecting the set of Electroencephalography (EEG) channels valid for determining the cognitive load of the subject.

What is claimed is:

1. A method for selecting a set of Electroencephalography (EEG) channels valid for determining a cognitive load of a subject, the method comprising:

receiving, by a processor, EEG signals obtained from a plurality of EEG channels associated with a subject performing one or more cognitive tasks, wherein the plurality of EEG channels are connected to a low resolution EEG device;

decomposing, by the processor, the EEG signals into a time-frequency domain;

extracting, by the processor, time-frequency features of the decomposed EEG signals for each of multiple frequency bands of each EEG channel of the plurality of EEG channels, wherein the time-frequency features include at least one of a maximum energy value, a minimum energy value, an average energy value, a maximum frequency value, a minimum frequency value, or an average frequency value, and wherein the multiple frequency bands of each of the EEG channels of the plurality of EEG channels include alpha, beta, theta, and delta;

deriving, by the processor, a weight for each time-frequency feature associated with each EEG channel of the plurality of EEG channels using a statistical learning technique;

assigning, by the processor, a binary value for each EEG channel of the plurality of EEG channels using the weight of each time-frequency feature associated with each EEG channel of the plurality of EEG channels, wherein the binary value of each EEG channel of the plurality of EEG channels is equal to 1 when the weight associated with the maximum energy value, the minimum energy value, the average energy value, the maximum frequency value, the minimum frequency value, and the average frequency value of each EEG channel of the plurality of EEG channels is greater than a threshold value and wherein the binary value of each EEG channel of the plurality of EEG channels is equal to 0 when the weight associated with the maximum energy value, the minimum energy value, the average energy value, the maximum frequency value, the minimum frequency value, and the average frequency value of each EEG channel of the plurality of EEG channels is less than or equal to the threshold value;

computing, by the processor, a first intersection of the binary value of each EEG channel of the plurality of EEG channels corresponding to the maximum energy value and the average energy value, a second intersection of the binary value of each EEG channel of the plurality of EEG channels corresponding to the minimum energy value and the average energy value, a third intersection of the binary value of each EEG channel of the plurality of EEG channels corresponding to the maximum frequency value and the average frequency value, and a fourth intersection of the binary value of each EEG channel of the plurality of EEG channels corresponding to the minimum frequency value and the average frequency value, wherein computation of the first intersection, the second intersection, the third intersection, and the fourth intersection is performed for binary values of the plurality of EEG channels corresponding to time frequency features associated with the multiple frequency bands;

computing, by the processor, a first union of the first intersection and the second intersection, and a second union of the third intersection and the fourth intersection;

computing, by the processor, a third union of the first union and the second union, wherein the third union represents the selected set of EEG channels and corresponding positions, on a head of the subject; and determining, by the processor, cognitive load of the subject based on power and frequency changes for the alpha and theta frequency bands of the selected set of EEG channels for a predefined time, wherein the selected set of EEG channels maximize separation of the cognitive load between a low load cognitive task and a high load cognitive task.

2. The method of claim 1, wherein the EEG signals are initially processed to remove one or more artifacts from the EEG signals after being received and prior to decomposing.

3. The method of claim 1, wherein the plurality of EEG channels are connected to the low resolution EEG device comprising a maximum of 10 to 20 EEG channels.

4. The method of claim 1, wherein the cognitive tasks comprise low load cognitive tasks or high load cognitive tasks.

5. The method of claim 1, wherein the binary value is assigned to the at least one frequency band of each EEG channel of the plurality of EEG channels using the weight associated with each time-frequency feature of each EEG channel of the plurality of EEG channels.

6. The method of claim 1, wherein the binary value equal to 1 represents a valid EEG channel and the binary value equal to 0 represents a not valid EEG channel.

7. The method of claim 1, wherein the statistical learning technique is at least one of a connectionist framework based Adaptive Neural Network technique, a Maximal Information Coefficient (MIC) based technique, a minimum Redundancy Maximum Relevance (mRMR) feature selection technique, or a Hilbert-Schmidt Independence Criterion Least absolute shrinkage and selection operator technique (HSIC Lasso).

8. The method of claim 1, wherein the third union representing the selected set of EEG channels valid to determine the cognitive load of the subject are assigned binary values equal to 1.

9. The method of claim 1, further comprising determining a weighted channel activation index for each EEG channel of the plurality of EEG channels to determine a discrimination power of each EEG channel of the plurality of EEG channels, wherein the weighted channel activation index is computed using binary values for each EEG channel of the plurality of EEG channels computed for a plurality of subjects and a maximum of F values as a weighting factor, wherein the F values represent a ratio of between group variability and within group variability, and the F values are computed using Analysis of Variance (ANOVA) analysis, and the F values are greater than zero.

10. A system for selecting a set of Electroencephalography (EEG) channels valid for determining a cognitive load of a subject, the system comprising:
a processor; and
a memory coupled to the processor, wherein the processor executes programmed instructions stored in the memory to:
receive EEG signals obtained from a plurality of EEG channels associated with a subject performing one or more cognitive tasks, wherein the plurality of EEG channels are connected to a low resolution EEG device;

decompose the EEG signals into a time-frequency domain;

extract time-frequency features of the decomposed EEG signals for each of multiple frequency bands of each EEG channel of the plurality of EEG channels, wherein the time-frequency features include at least one of a maximum energy value, a minimum energy value, an average energy value, a maximum frequency value, a minimum frequency value, or an average frequency value, and wherein the multiple frequency bands of each of the EEG channels of the plurality of EEG channels include alpha, beta, theta, and delta;

derive a weight for each time-frequency feature associated with each EEG channel of the plurality of EEG channels using a statistical learning technique;

assign a binary value for each EEG channel of the plurality of EEG channels using the weight of each time-frequency feature associated with each EEG channel of the plurality of EEG channels, wherein the binary value of each EEG channel of the plurality of EEG channels is equal to 1 when the weight associated with the maximum energy value, the minimum energy value, the average energy value, the maximum frequency value, the minimum frequency value, and the average frequency value of each EEG channel of the plurality of EEG channels is greater than a threshold value and wherein the binary value of each EEG channel of the plurality of EEG channels is equal to 0 when the weight associatedwith the maximum energy value, the minimum energy value, the average energy value, the maximum frequency value, the minimum frequency value, and the average frequency value of each EEG channel of the plurality of EEG channels is less than or equal to the threshold value;

compute a first intersection of the binary value of each EEG channel of the plurality of EEG channels corresponding to the maximum energy value and the average energy value, a second intersection of the binary value of each EEG channel of the plurality of EEG channels corresponding to the minimum energy value and the average energy value, a third intersection of the binary value of each EEG channel of the plurality of EEG channels corresponding to the maximum frequency value and the average frequency value, and a fourth intersection of the binary value of each EEG channel of the plurality of EEG channels corresponding to the minimum frequency value and the average frequency value, wherein computation of the first intersection, the second intersection, the third intersection, and the fourth intersection is performed for binary values of the EEG channels of the plurality of EEG channels corresponding to time frequency features associated with the multiple frequency bands;

compute a first union of the first intersection and the second intersection, and a second union of the third intersection and the fourth intersection;

compute a third union of the first union and the second union, wherein the third union represents the selected set of EEG channels and corresponding positions, on a head of the subject; and determine cognitive load of the subject based on power and frequency changes for the alpha and theta frequency bands of the selected set of EEG channels for a predefined time, wherein the selected set of EEG channels maximize separation of the cognitive load between a low load cognitive task and a high load cognitive task.

11. The system of claim 10, wherein the EEG signals are initially processed to remove one or more artifacts from the EEG signals after being received and prior to decomposing.

12. The system of claim 10, wherein the binary value equal to 1 represents a valid EEG channel and the binary value equal to 0 represents a not valid EEG channel.

13. The system of claim 10, wherein the statistical learning technique includes at least one of a connectionist framework based Adaptive Neural Network technique, a Maximal Information Coefficient (MIC) based technique, a minimum Redundancy Maximum Relevance (mRMR) feature selection technique, or a Hilbert-Schmidt Independence Criterion Least absolute shrinkage and selection operator technique (HSIC Lasso).

14. The system of claim 10, wherein the processor executes programmed instructions stored in the memory to determine a weighted channel activation index for each EEG channel of the plurality of EEG channels to determine a discrimination power of each EEG channel of the plurality of EEG channels, wherein the weighted channel activation index is computed using binary values for each EEG channel of the plurality of EEG channels computed for a plurality of subjects and a maximum of F values as a weighting factor, wherein the F values represent a ratio of between group variability and within group variability, and the F values are computed using Analysis of Variance (ANOVA) analysis, and the F values are greater than zero.

15. A non-transitory computer-readable medium comprising a computer program executable by at least one processor for selecting a set of Electroencephalography (EEG) channels valid for determining a cognitive load of a subject, the computer program comprising:
  a program code for receiving EEG signals obtained from a plurality of EEG channels associated with a subject performing one or more cognitive tasks, wherein the plurality of EEG channels are connected to a low resolution EEG device;
  a program code for decomposing the EEG signals into a time-frequency domain;
  a program code for extracting time-frequency features of the decomposed EEG signals for each of multiple frequency bands of each EEG channel of the plurality of EEG channels, wherein the time-frequency features include at least one of a maximum energy value, a minimum energy value, an average energy value, a maximum frequency value, a minimum frequency value, or an average frequency value, and wherein the multiple frequency bands of each of the EEG channels of the plurality of EEG channels include alpha, beta, theta, and delta;
  a program code for deriving a weight for each time-frequency feature associated with each EEG channel of the plurality of EEG channels using a statistical learning technique;
  a program code for assigning a binary value for each EEG channel using the weight of each time-frequency feature associated with each EEG channel of the plurality of EEG channels, wherein the binary value of each EEG channel of the plurality of EEG channels is equal to 1 when the weight associated with the maximum energy value, the minimum energy value, the average energy value, the maximum frequency value, the minimum frequency value, and the average frequency value of each EEG channel of the plurality of EEG channels is greater than a threshold value and wherein the binary value of each EEG channel of the plurality of EEG channels is equal to 0 when the weight associated with the maximum energy value, the minimum energy value, the average energy value, the maximum frequency value, the minimum frequency value, and the average frequency value of each EEG channel of the plurality of EEG channels is less than or equal to the threshold value;
  a program code for computing a first intersection of the binary value of each EEG channel of the plurality of EEG channels corresponding to the maximum energy value and the average energy value, a second intersection of the binary value of each EEG channel of the plurality of EEG channels corresponding to the minimum energy value and the average energy value, a third intersection of the binary value of each EEG channel of the plurality of EEG channels corresponding to the maximum frequency value and the average frequency value, and a fourth intersection of the binary value of each EEG channel of the plurality of EEG channels corresponding to the minimum frequency value and the average frequency value, wherein computation of the first intersection, the second intersection, the third intersection, and the fourth intersection is performed for binary values of the plurality of EEG channels corresponding to time frequency features associated with the multiple frequency bands;
  a program code for computing a first union of the first intersection and the second intersection, and a second union of the third intersection and the fourth intersection;
  a program code for computing a third union of the first union and the second union, wherein the third union represents the selected set of EEG channels and corresponding positions, on a head of the subject; and
  a program code for determining cognitive load of the subject based on power and frequency changes for the alpha and theta frequency bands of the selected set of EEG channels for a predefined time, wherein the selected set of EEG channels maximize separation of the cognitive load between a low load cognitive task and a high load cognitive task.

16. The medium of claim 15, wherein the EEG signals are initially processed to remove one or more artifacts from the EEG signals after being received and prior to decomposing.

17. The medium of claim 15, wherein the binary value equal to 1 represents a valid EEG channel and the binary value equal to 0 represents a not valid EEG channel.

18. The medium of claim 15, wherein the statistical learning technique includes at least one of a connectionist framework based Adaptive Neural Network technique, a Maximal Information Coefficient (MIC) based technique, a minimum Redundancy Maximum Relevance (mRMR) feature selection technique, or a Hilbert-Schmidt Independence Criterion Least absolute shrinkage and selection operator technique (HSIC Lasso).

19. The medium of claim 15, wherein the computer program further includes a program code for determining a weighted channel activation index for each EEG channel of the plurality of EEG channels to determine a discrimination power of each EEG channel of the plurality of EEG channels, wherein the weighted channel activation index is computed using binary values for each EEG channel of the plurality of EEG channels computed for a plurality of subjects and a maximum of F values as a weighting factor, wherein the F values represent a ratio of between group variability and within group variability, and the F values are computed using Analysis of Variance (ANOVA) analysis, and the F values are greater than zero.

* * * * *